(12) United States Patent
Christensen et al.

(10) Patent No.: US 8,439,833 B2
(45) Date of Patent: May 14, 2013

(54) OPHTHALMIC STRUCTURE

(75) Inventors: James Marlow Christensen, Glendora, CA (US); D. Michael Colvard, Encino, CA (US)

(73) Assignee: Oasis Medical, Inc., Glendora, CA (US)

( * ) Notice: Subject to any disclaimer, the term of this patent is extended or adjusted under 35 U.S.C. 154(b) by 0 days.

(21) Appl. No.: 13/275,685

(22) Filed: Oct. 18, 2011

(65) Prior Publication Data
US 2013/0096386 A1    Apr. 18, 2013

(51) Int. Cl.
*A61B 1/32* (2006.01)

(52) U.S. Cl.
USPC .......................................................... 600/236

(58) Field of Classification Search .................. 606/107, 606/4–6; 604/294, 302; 600/201, 206, 210, 600/233, 236, 237, 238, 239, 242, 243
See application file for complete search history.

(56) References Cited

U.S. PATENT DOCUMENTS

| | | | | |
|---|---|---|---|---|
| 2,053,868 A * | 9/1936 | Grosso | ............................ | 600/233 |
| 2,845,925 A * | 8/1958 | Jayle | ............................ | 600/233 |
| 4,037,589 A * | 7/1977 | McReynolds | .................. | 600/209 |
| 4,321,916 A | 3/1982 | McKee | | |
| 4,640,273 A * | 2/1987 | Greene et al. | .................. | 128/861 |
| 4,991,567 A | 2/1991 | McCuen, II et al. | | |
| 5,427,088 A | 6/1995 | Graether | | |
| 5,441,040 A * | 8/1995 | Williams, Jr. | .................. | 600/236 |
| 5,634,884 A | 6/1997 | Graether | | |
| 5,653,753 A | 8/1997 | Brady et al. | | |
| 5,851,177 A * | 12/1998 | Koch | ............................ | 600/206 |
| 6,190,312 B1 * | 2/2001 | Fowler, Jr. | ..................... | 600/231 |
| 6,332,866 B1 | 12/2001 | Grieshaber et al. | | |
| 6,648,819 B2 * | 11/2003 | Lee | ................................. | 600/236 |
| 7,985,180 B2 | 7/2011 | Brown | | |
| 2002/0055753 A1 | 5/2002 | Silvestrini | | |
| 2003/0092970 A1 | 5/2003 | Lee | | |
| 2008/0243139 A1 | 10/2008 | Dusek | | |
| 2008/0269888 A1 | 10/2008 | Malyugin | | |

FOREIGN PATENT DOCUMENTS

| | | |
|---|---|---|
| DE | 9320127 U1 | 5/1994 |
| RU | 14505 U1 | 2/2000 |
| RU | 14506 U1 | 2/2000 |
| WO | WO 00/30566 | 6/2000 |

* cited by examiner

*Primary Examiner* — Eduardo C Robert
*Assistant Examiner* — David Comstock
(74) *Attorney, Agent, or Firm* — Greenberg Traurig, LLP

(57) ABSTRACT

A ring for dilating a pupil during an ophthalmic procedure includes a series of spaced supports for engaging an iris perimeter. The supports are plate elements which form an open pocket directed outwardly for engaging the iris. The sides of the ring form a primary plane, and the plates are located in respective planes above and below the primary plane. The outer periphery of the top and bottom plates forms a lip feature which is the opening to the pocket which retains the iris.

23 Claims, 3 Drawing Sheets

OPHTHALMIC STRUCTURE

FIELD OF THE DISCLOSURE

The present disclosure relates to a structure used in an ophthalmic surgical procedure. There are various ophthalmic procedures that require the dilation of the pupil. It is desirable to extend the pupil during the procedure to provide the surgeon with a wide view of the lens. Known techniques for extending and pulling back the iris cause damage to iris tissue.

Patients who have a small pupil pose a major problem and challenge during ophthalmic surgery. When such a patient has cataract or vitreo-retinal surgery and their pupil cannot be easily dilated by mydriatic eye drops, the surgery becomes difficult unless the pupil can be mechanically dilated.

Current styles of iris supporting rings tend to snag the incision into the eye as the rings are being removed from the eye after use. This not only make removal more difficult, but it also can lead to the ring scrapping against the endothelial cells lining the inside of the cornea as the surgeon attempts to free the snagged ring.

Pharmacological approaches for managing a small pupil during cataract surgery have limitations. A significant problem for the surgeon is decreased visualization, iris trauma due to incarceration into the wound, iris chafing, pupillary margin damage by needles and others.

For example, cataracteous lenses are typically replaced in a procedure commonly referred to as phacoemulsification. For this procedure the lens is broken up with an instrument, typically with an ultrasonically driven tool. To safely perform this procedure a surgeon needs to visualize the entire cataracteous lens.

There is need for a better technique and device for safely dilating the iris.

SUMMARY

A structure which is a ring is used to maintain a pupil in an extended open position during an ophthalmic procedure.

In one form the ring has a series of spaced supports for engaging an iris perimeter. The supports are elements with an open pocket directed outwardly for engaging the iris. Each pocket is formed by two plates which are spaced apart from each other.

In another form the ring forms a primary plane. Plates forming the open pockets are located in two additional planes spaced apart from each other with one plane located above the primary plane and the second plane located below the primary plane. The plates are substantially parallel to each other in their respective planes, and provide an open pocket directed outwardly away from the center of the ring.

The disclosure is further described with reference to the accompanying drawings.

DRAWINGS

DETAILED DESCRIPTION

Figure 1:
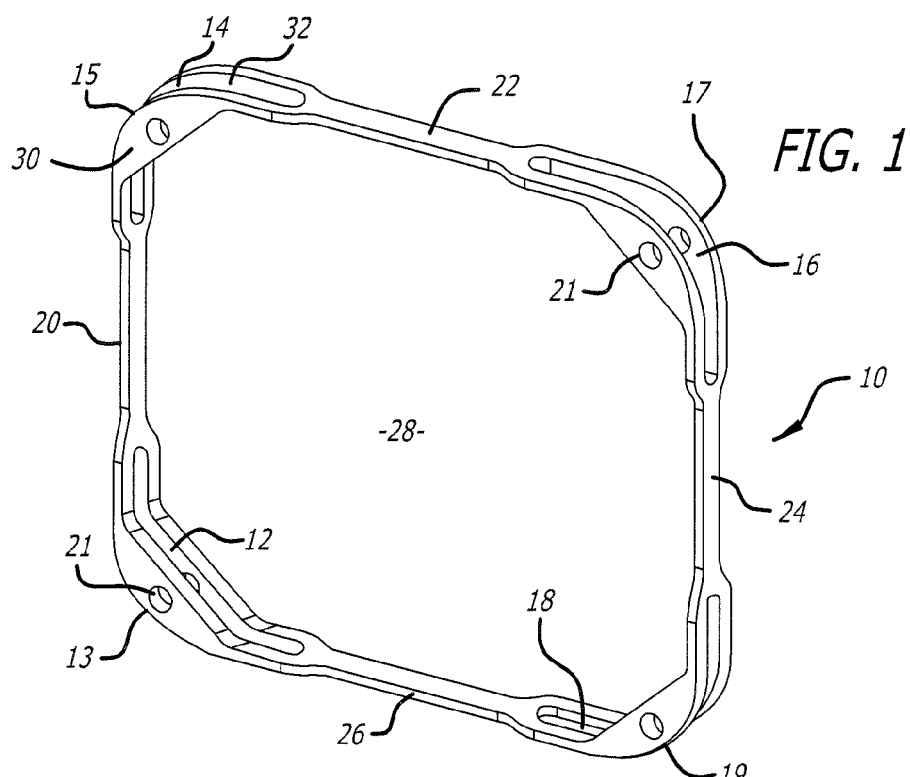
FIG. 1 is a perspective view of a ring of the present disclosure.

The novel features of this disclosure, as well as the disclosure itself, both as to its structure and its operation, will be best understood from the accompanying drawings, taken in conjunction with the accompanying description. Terminology is used in the following description for convenience only and is not limiting. In the drawings, like numerals are used to indicate like elements.

Figure 2:
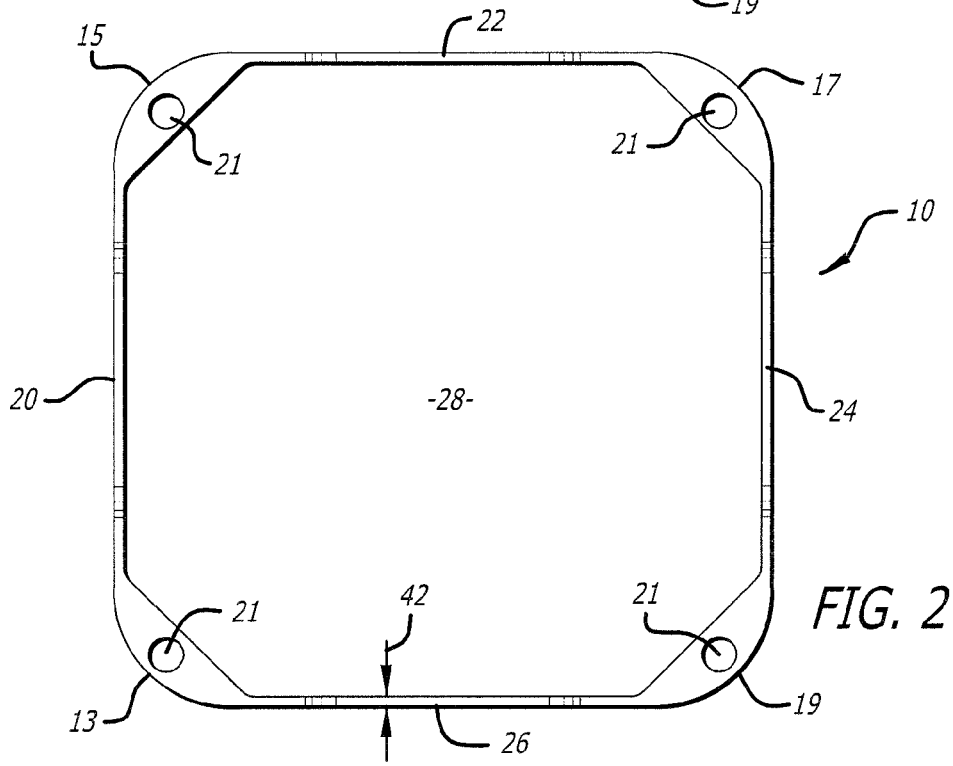
FIG. 2 is an top view showing the ring.
Figure 3:
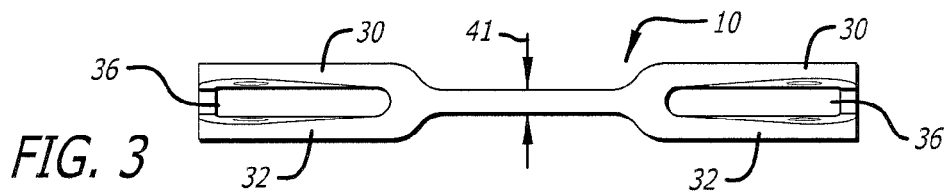
FIG. 3 is a side view of the ring.

As shown in FIGS. 1, 2 and 3, this disclosure provides a flexible ring 10 which can be used to support the iris in an open configuration during surgery and be easily removed without snagging the edges of the incision during removal.

A structure for dilating a pupil during an ophthalmic procedure comprises a ring, the ring having a series of spaced supports for engaging an iris perimeter. The supports are pockets formed by two plates directed outwardly for engaging the iris. Between the pockets there is a connecting limb with an elongated axis. The connecting limb is bendable or flexible along its axis to permit bringing the pockets closer together when bent. The limb is narrower in a view when considered from a top of the structure, relative to a view when considered from the side of the structure.

In the described embodiment of this disclosure, ring 10 has a square formation with rounded corners 13, 15, 17 and 19. At each corner there is a top plate 30 which forms generally one plane of the ring and there is a bottom plate 32 which forms generally a second plane of the ring. These planes are generally above and below the primary plane of the ring formed by connecting limbs 20, 22, 24 and 26.

Together the outer periphery of the top plate and the bottom plate at each corner form a lip feature which is the entrance to the pockets 12, 14, 16 and 18 that will contain a portion of the iris to be supported in an open configuration. The outer periphery of the lips formed by the top and bottom plates are relatively curved or rounded so that the corners and edges are not sharp and will not damage the iris tissue.

Generally the top 30 and bottom 32 plates at each corner are parallel with each other. However, the top and bottom plates can be angled slightly from each other to provide a wider opening at the outer periphery of the ring so that the iris may be captured more easily in the pocket formed by the plates.

The pockets defined by the lip feature are located at each corner of the ring. Between each rounded corner there is a straight limb 20, 22, 24 and 26 joining the corners. The straight limbs are located between the first and second planes formed by the top and bottom plates.

Generally the top and bottom plates are respectively above and below the primary plane formed by the straight limbs. However, either the top or bottom plane can be coincident with the primary plane as long as the other plane is spaced apart from the primary plane in order to form a pocket.

Figure 4:
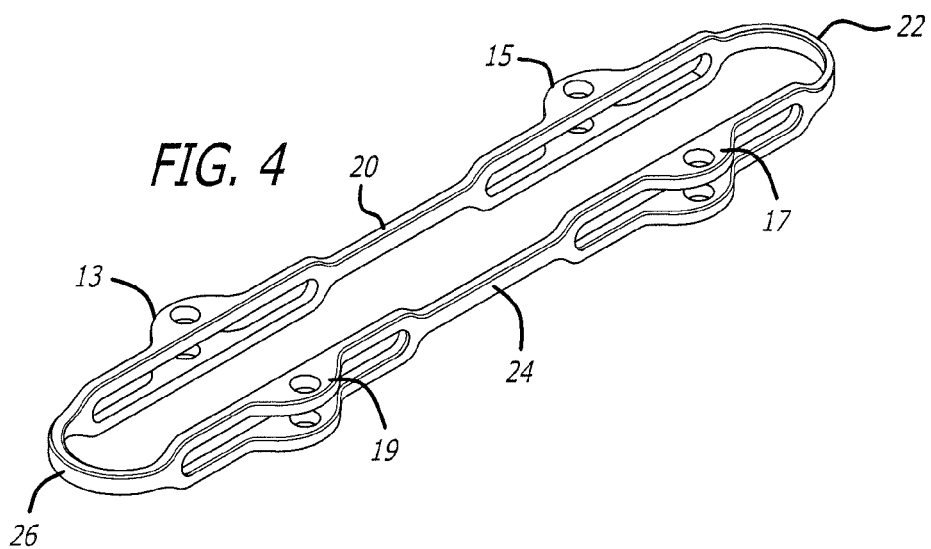
FIG. 4 is a perspective view of the ring in a folded condition for insertion into the eye.

In the described embodiment, the width 42 of the straight limbs is smaller than the height 41 of the straight limbs. This causes the limbs to flex in the preferred direction of the primary plane and results in the ring remaining between the first and second planes when the limbs are flexed as shown in FIG. 4. This is desirable in order to prevent contact of the ring with the inside surface of the cornea during flexure.

The four straight limbs 20, 22, 24 and 26 along with the four corners 13, 15, 17 and 19 circumscribe a central opening 28. When the ring is in place, the iris tissue is supported outside this central opening by the structures of the ring.

The ring can be folded by bringing an opposing pair of corners 13-17 or 15-19 together so that the ring can be inserted through a small incision made in the scleral portion of the eye. Alternatively, as shown in FIG. 4 the ring can be folded by bending an opposing pair of straight limbs 22-26 or 20-24 into an opposing U-shaped configuration so that adjacent pairs of corners 13-19 and 15-17 or 13-15 and 17-19 can come together and enable the ring to be inserted through a small incision.

Figure 5:
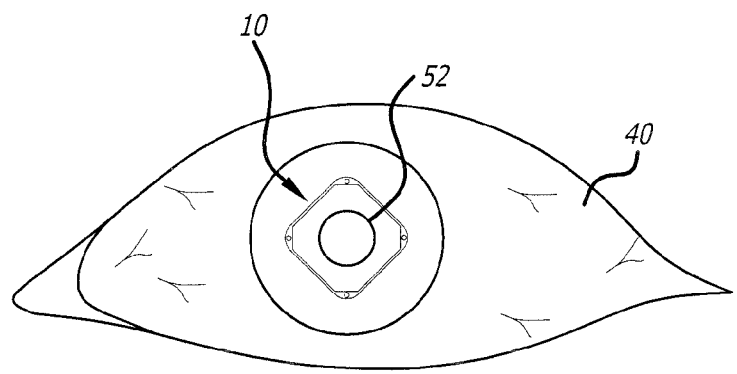
FIG. 5 is an illustration showing the ring placed on top of the iris tissue in the eye.
Figure 6:
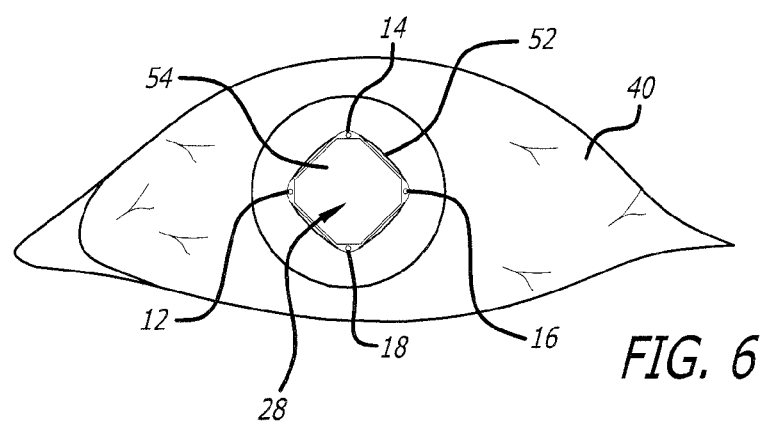
FIG. 6 is an illustration showing an iris being maintained in an enlarged position by the ring in order to provide a greater pupillary opening.

Once inside the eye 40 the ring 10 is unfolded and placed on top of the iris 52 as shown in FIG. 5. Using a Lester Hook, or other similar instrument, the ring can be manipulated using the holes placed in the top and bottom plates at each corner of the ring. As shown in FIG. 6 the ring can then be positioned so that the edge of the iris is captured by pockets 12, 14, 16 and 18 at each corner of the ring and the iris rests on the straight limbs 20, 22, 24, and 26 thereby stretching and holding the iris in a more open configuration.

The ring maintains the iris in an extended position during an ophthalmic procedure. This provides a large center opening 28 that provides a wide view of the ocular chamber and enables ophthalmic procedures such as phacoemulsification to be safely performed.

Following surgery, a Lester Hook, or other similar instrument, can be used to grasp the ring by the holes placed in the top and bottom plates at each corner of the ring or by the straight limbs and pull the ring back through the small incision and out of the eye. Since the top and bottom plates transition smoothly into the straight limbs and there are no protruding features at the corners of the ring, the ring will slip easily out of the eye without snagging on the edges of the corneal incision or other intraocular tissues.

The ring is formed by multiple sides with a corner area at the intersection of each pair of sides which defines the outer perimeter. The corner area has a rounded outer profile and contains a pocket formed by an upper and a lower plate which is directed outwardly for engaging the iris. An aperture in the plates forming the corners of the ring is included for manipulating the ring.

In one form the ring is shaped as a rectangle, such as a square. There are four pockets, one each located at a respective corner. The ring can also be formed in other shapes such as a triangle with three sides, a pentagon with five sides, or other similar configurations. In each of these shapes the ring defines an outer perimeter, and at each corner there is a pocket directed outwardly for engaging the iris. There can be as many pockets as there are respective corners.

As shown in FIG. 3 each pocket 12, 14, 16 and 18 has a space 36 between respective top 30 and bottom 32 plates that receives and captures iris tissue. The pocket design provides an easy means of capturing iris tissue. The flexibility of the material forming the ring allows the straight limbs to be deformed in order for the pockets to be manipulated so that they can capture the iris tissue. The elasticity of the iris tissue assists in maintaining the position of the ring relative to the center of the eye.

Figure 7:
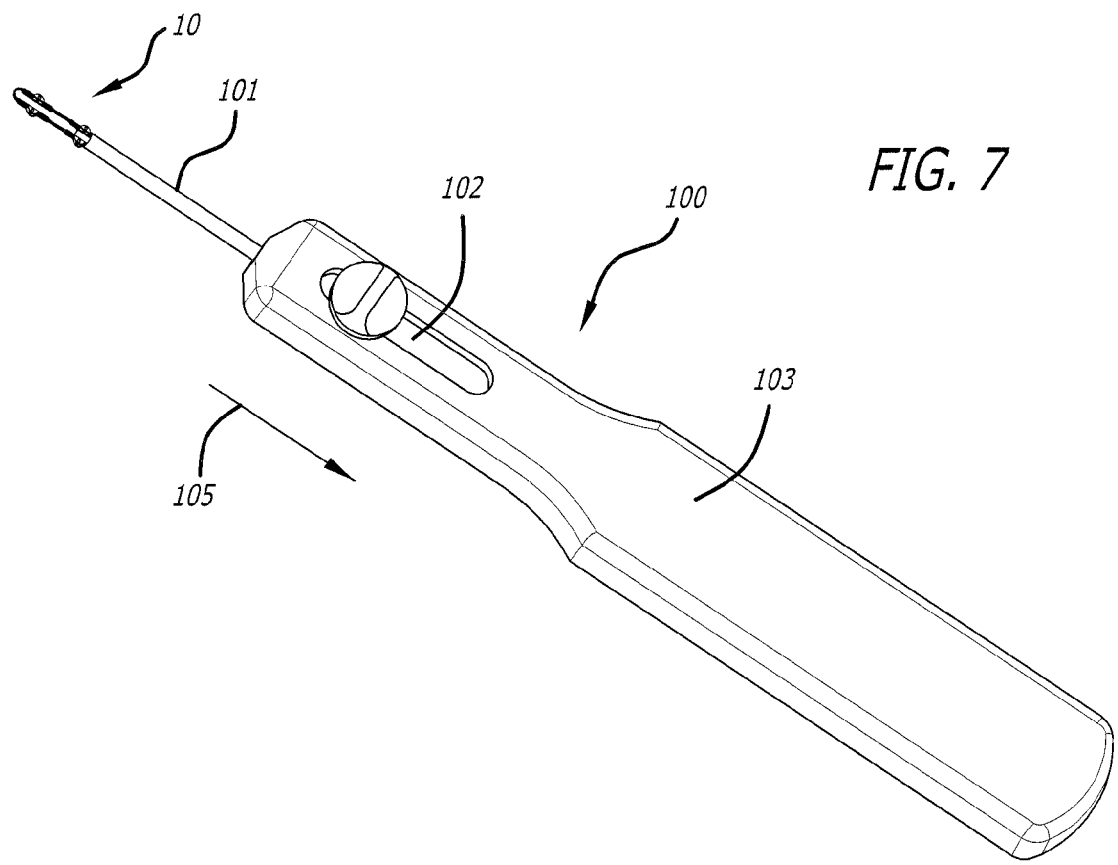
FIG. 7 is a perspective view of an inserter with the loaded ring being ejected from the end of the inserter.

FIG. 7 shows the inserter 100 used to insert a ring 10 into a patient's eye. The ring 10 is loaded into the inserter 100 by drawing it into the tip of the inserter tube 101 using a hook attached to the inserter slide mechanism 102. The inserter 100 is comprised of a tube 101 attached to an inserter handle 103.

The ring 10 is drawn into the inserter 100 by a hook attached to the slide mechanism 102. The ring is folded by the sides of the inserter tube tip as it is drawn into the inserter tube. The ring is drawn into the inserter tube by moving the inserter mechanism 102 in the direction indicated by the arrow 105 until the ring is completely contained within the tube.

Figure 8:
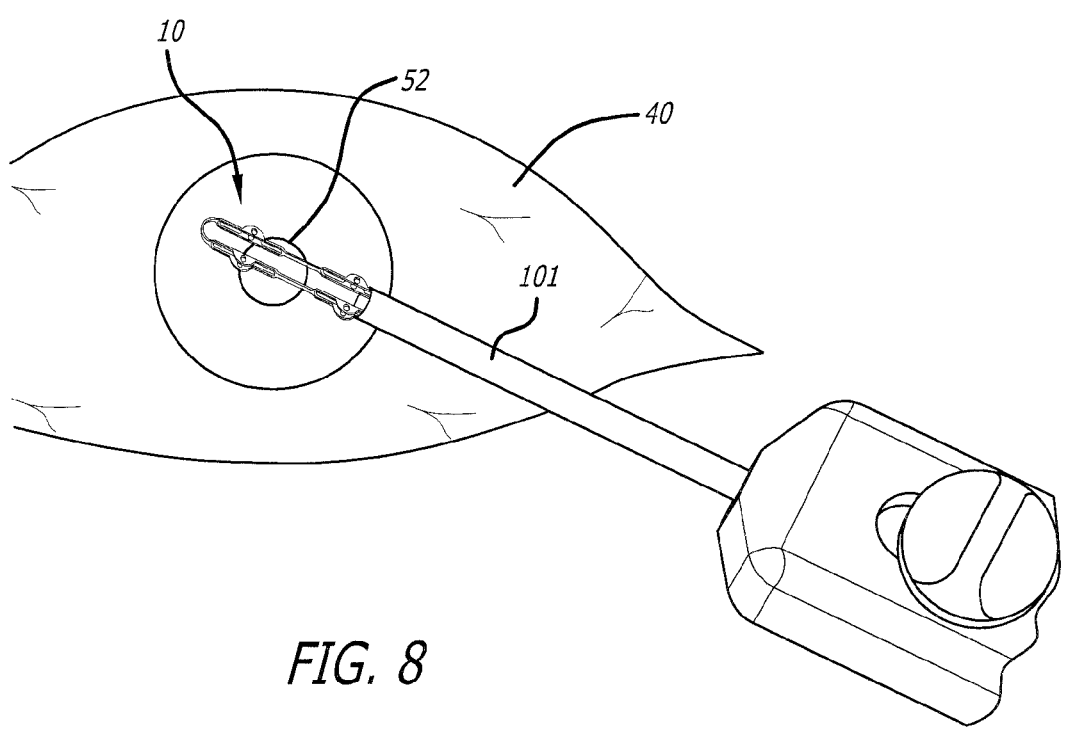
FIG. 8 is an illustration of a portion of the inserter during the insertion of the loaded ring into the eye.

After the insertion tube 101 is loaded with the ring, the tube is inserted into the patient's eye through a small incision. The tube is positioned over the iris as shown in FIG. 8 and the ring is ejected out of the tube by moving the inserter mechanism 102 in the direction opposite that indicated by the arrow 105. Once in the eye, the inserter tube 101 is withdrawn from the eye and a Lester hook is used to manipulate the ring to capture iris tissue. The ring 10 provides balanced stretching and gently holds the iris tissue in place.

When the procedure is complete the ring 10 can be removed from the eye. The inserter can be placed back through the small incision into the eye and the ring can be drawn back into the inserter. Alternatively, the ring can be pulled out of the eye through the small incision using a Lester hook.

Advantages of the disclosed ring 10 include the following features: There are no features that can snag tissues in the eye or the edges of the incision in the eye used for insertion or removal of the ring. There are no sharp or pointed edges or surfaces that can damage to the eye. Equidistant positioning of the pockets holds the iris tissue, ensuring correct position of the iris and preventing the effects of an overstretched iris that are often observed in the incorrect positioning of other iris retractors. The ring uniformly supports the iris over the entire outer periphery of the ring since the supported iris lies against the straight sides 20, 22, 24 and 26 of the ring. Additional incisions are not required. Sufficient room is available to perform surgical procedures through the central opening of the ring. The ring includes straight limbs or sides between the pockets. The limbs or sides may be straight. In some embodiments they have a configuration that allows for easier bending at least in the overall plane in which the limbs collectively extend. This can be for instance by having one or more accordion shape or features in structure of the limbs. In other cases the sides or limbs can be notched and/or crimped at one or more points on their structure. In yet other forms one or more of the limbs or sides can have a relatively curved shape considered in the overall top plane.

Tapered or wider pockets can be formed by tapering the inside surface of at least one plate of the pair at each corner. Alternatively, the entire plate forming the top and/or bottom surfaces are relatively tapered. Overall this structure provides a sufficiently wide opening to capture the iris while maintaining a compact overall form of the ring. This minimizes contact with the inside of the cornea as it curves down to meet up with the periphery of the iris.

The shape of the straight limbs acts to minimize the flexing of the ring in a way that it contacts the inside of the cornea. Having a cross-sectional structure and orientation of thick and thin sections of limbs causes the flexure of the ring to be in the plane of the ring. This can also be caused by placing crimp structures in the limbs and along the limbs to also cause preferred flexure directions of the limbs.

Overall the ring of the disclosure has an absence of features on the ring that could snag the incision or tissues inside the eye upon removal, and in part this is achieved by the one-piece design. of the ring.

The ring 10 is preferably constructed from a molded plastic material such as polyethylene or polypropylene. However, the iris supporting ring can be machined or molded from other suitable plastic such as polyurethane, polycarbonate, nylon, etc., or from a suitable elastomeric such as silicone, or from a suitable metal such as a hardened stainless steel or nitinol which can tolerate the folding required to place the ring through a small incision. Other plastic, elastomeric, or metallic materials, or composite material made from these materials may also be usable.

Polyethylene and polypropylene made the ring tough and flexible. These materials permit for a molded ring which is able to be bent and deformed a number of times without breaking. When inserted into the eye after being folded in the inserter, the rings recover their shape relatively easily and effectively.

The ring can also be formed from plastics which can be 'frozen' in a deformed condition. The preferred deformed condition would be with the ring collapsed together as shown in FIG. 4 so that the ring could be placed through a small incision. Once the frozen ring is in the eye, the fluids in the eye will warm the ring and allow it to return to its original condition.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure.

We claim:

1. A structure for dilating a pupil during an ophthalmic procedure, comprising a ring, the ring being closed upon itself and not having free ends, and having an inner periphery and an outer periphery, a series of spaced supports for engaging an iris perimeter, the supports being elements with an open pocket directed outwardly for engaging the iris, each pocket formed by two plates, the plates being spaced apart to form the opening of each pocket, and the open pocket extending as an unimpeded space from the outer periphery through to the inner periphery of the ring.

2. The structure of claim 1, wherein said ring is shaped as a rectangle.

3. The structure of claim 1, wherein said ring is shaped as a square.

4. The structure of claim 1, wherein said ring has a pocket located at corners of the ring.

5. The structure of claim 1, wherein the ring includes straight limbs between respective pockets.

6. The structure of claim 1 wherein the ring includes at least an aperture in the plates.

7. The structure of claim 1 wherein the ring is formed by multiple sides, and including a corner area at the intersection of each pair of sides, the corner having a rounded outer profile, and including an aperture in the material of the ring in the vicinity of the corner.

8. The structure of claim 1 including a limb between the respective pockets, and wherein the limb is located in a plane different to the respective two plates of each pocket.

9. The structure of claim 1 including a limb between the respective pockets, and wherein the limb is located in a plane between the respective two plates of each pocket.

10. The structure of claim 9 including a curved transition area connecting the limb and the respective plates.

11. The structure of claim 1 including a limb between the respective pockets, and wherein the limb is located in a plane of one of the respective two plates of each pocket.

12. The structure of claim 1 wherein the plates include a taper between their spaced apart structure such that the outwardly directed open ends of the spaced apart plates are wider than the space between the plates at the inner periphery open ends.

13. The structure of claim 1 wherein the ring is molded from a material selected from a group consisting of polyethylene and polypropylene.

14. A structure for dilating a pupil during an ophthalmic procedure, comprising a ring, the ring having a series of spaced supports for engaging an iris perimeter, the supports being pocket features formed by the outer periphery of a top lip and a bottom lip forming an open pocket directed outwardly for engaging the iris and open to the inner periphery of the ring, and wherein the ring is defined an outer perimeter, and each pocket is located at a respective corner of the perimeter, and between first and second pockets there being a connecting straight limb with an elongated axis, the connecting straight limb being bendable along its axis, thereby to permit bringing the two pockets relatively closer together when bent, the connecting limb being for bending on itself thereby to bring two corners closer together and permit the location of the structure in a bore of a tool, the tool being for use for insertion of the ring into position about the iris perimeter when the ring is ejected from the tool bore, and the ring after ejection being straightened along the connecting limb to re-form as a straight limb.

15. The structure of claim 14, wherein said ring is shaped as a rectangle and includes corners defined at the intersection of limbs directed in a transverse direction relative to each other, and wherein the pocket features are formed at each corner.

16. The structure of claim 15, wherein said ring has four pockets, and respective straight limbs between each corner.

17. The structure of claim 14, wherein said ring is shaped as a square, and includes corners defined at the intersection of limbs directed in a transverse direction relative to each other, and wherein the pocket features are formed at each corner.

18. The structure of claim 14, wherein the pockets at each respective corner are structured not to bend when the corners are brought closer together.

19. The structure of claim 14, wherein the interface between the pockets at each respective corner and the adjacent straight limbs are structured to bend when the corners are brought closer together.

20. A structure for dilating a pupil during an ophthalmic procedure, comprising a ring, the ring being closed upon itself and not having free ends, the ring having a series of spaced supports for engaging an iris perimeter, the supports being plates forming an open pocket directed outwardly for engaging the iris with an opening through the pocket to the inner periphery of the ring, and between the pockets there being a straight connecting limb with an elongated axis, the connecting straight limb being bendable along its axis during location and removal from the operative position with the iris, thereby to permit bringing the pockets relatively closer together when bent, and the limb being narrower in a view when considered from a top of the structure, relative to a view when considered from the side of the structure.

21. A structure for enlarging an iris opening during an ophthalmic procedure, comprising a ring, the ring being closed upon itself and not having free ends, the ring having a series of spaced pockets for engaging an iris perimeter, the pockets being formed in an outer perimeter of a top plate and a bottom plate, the outer perimeter of the plates forming a lip feature which forms the opening to the pocket, the lips being spaced apart to form an opening of each pocket and the pocket being open to the inner periphery of the ring, and each pocket being directed outwardly for engaging the iris, there being a straight connecting limb between adjacent pockets, the limb having an elongated axis, the connecting straight limb being bendable along its axis thereby to permit the ring to become elongated when bent.

22. A structure for dilating a pupil during an ophthalmic procedure, comprising a ring, the ring being closed upon itself and not having free ends, a series of spaced supports for engaging an iris perimeter, the supports being elements with an open pocket directed outwardly for engaging the iris, each pocket formed by two plates, the plates being spaced apart to form the opening of each pocket, and defining a first height between the top of first plate and a bottom of a second plate, the opening extending completely between the plates from the outer periphery through to the inner periphery of the ring, and the ring includes straight limbs between respective pockets and the straight limbs extend in height less than the first height.

23. A structure for dilating a pupil during an ophthalmic procedure, comprising a ring, the ring having an inner periphery and an outer periphery, the ring being closed upon itself and not having free ends, a series of spaced supports for engaging an iris perimeter, the supports being elements with an open pocket directed outwardly for engaging the iris, each pocket formed by two plates, the plates being spaced apart to form the opening of each pocket, the opening extending completely between the plates from the outer periphery through to the inner periphery of the ring, and the ring includes straight limbs between respective pockets, the straight limbs extending in length longer than corner areas having the spaced supports, and the outer periphery being formed with four sides having rounded corners, the spaced supports being located solely at the rounded corners, and the inner periphery being essentially straight lines and ending in thickened areas at the rounded corners where the spaced supports are located.

* * * * *